US009423393B2

(12) United States Patent
    Sin

(10) Patent No.: US 9,423,393 B2
(45) Date of Patent: Aug. 23, 2016

(54) ANALYTICAL TEST CARTRIDGE; AND, METHODS

(71) Applicant: International Technidyne Corporation, Piscataway Township, NJ (US)

(72) Inventor: Kee Van Sin, Lino Lakes, MN (US)

(73) Assignee: International Technidyne Corporation, Piscataway Township, NJ (US)

( * ) Notice: Subject to any disclaimer, the term of this patent is extended or adjusted under 35 U.S.C. 154(b) by 0 days.

(21) Appl. No.: 14/193,180

(22) Filed: Feb. 28, 2014

(65) Prior Publication Data

US 2015/0064732 A1    Mar. 5, 2015

Related U.S. Application Data

(63) Continuation of application No. 12/535,589, filed on Aug. 4, 2009, now abandoned, which is a continuation of application No. 10/185,201, filed on Jun. 28, 2002, now Pat. No. 7,569,393.

(51) Int. Cl.
    *G01N 33/48*    (2006.01)
    *G01N 33/49*    (2006.01)

(52) U.S. Cl.
    CPC ... *G01N 33/4915* (2013.01); *Y10T 436/115831* (2015.01); *Y10T 436/116664* (2015.01); *Y10T 436/143333* (2015.01); *Y10T 436/144444* (2015.01); *Y10T 436/171538* (2015.01); *Y10T 436/193333* (2015.01); *Y10T 436/201666* (2015.01); *Y10T 436/204998* (2015.01); *Y10T 436/209163* (2015.01); *Y10T 436/2575* (2015.01)

(58) Field of Classification Search
    CPC .. G01N 33/4915; G01N 11/00; B01L 3/5027; Y10T 436/115831; Y10T 436/116664; Y10T 436/143333; Y10T 436/144444; Y10T 436/171538; Y10T 436/193333; Y10T 436/201666; Y10T 436/204998; Y10T 436/209163; Y10T 436/2575
    See application file for complete search history.

(56) References Cited

U.S. PATENT DOCUMENTS

| 4,000,972 A | 1/1977 | Braun et al. |
| RE30,007 E | 5/1979 | Steuer et al. |
| 4,443,408 A * | 4/1984 | Mintz ............................ 422/73 |
| 4,469,593 A | 9/1984 | Ishihara et al. |
| 4,484,135 A | 11/1984 | Ishihara et al. |

(Continued)

FOREIGN PATENT DOCUMENTS

| WO | WO 94/19683 | 9/1994 |
| WO | WO 00/40963 | 7/2000 |

OTHER PUBLICATIONS

Office Action for U.S. Appl. No. 10/210,661, mailed Nov. 20, 2003.

(Continued)

*Primary Examiner* — Lyle Alexander
*Assistant Examiner* — Robert Eom

(57) ABSTRACT

An analytical test cartridge is provided. The analytical test cartridge can be used for medical analyses of liquid samples removed from a patient, for example blood. The analytical test cartridge is configured to provide for titration experiments. An example of a titration experiment that can be performed with the arrangement, is titration of heparin with protamine. Methods of assembly and use are provided.

9 Claims, 6 Drawing Sheets

(56) References Cited

U.S. PATENT DOCUMENTS

| | | | |
|---|---|---|---|
| 4,686,479 | A | 8/1987 | Young et al. |
| 4,752,449 | A | 6/1988 | Jackson et al. |
| 4,793,285 | A | 12/1988 | Marshall |
| 4,818,361 | A | 4/1989 | Burgess et al. |
| 5,112,455 | A | 5/1992 | Cozzette et al. |
| 5,223,433 | A | 6/1993 | Deetz et al. |
| 5,232,667 | A | 8/1993 | Hieb et al. |
| 5,236,570 | A | 8/1993 | Ma et al. |
| 5,325,853 | A | 7/1994 | Morris et al. |
| 5,384,031 | A | 1/1995 | Anderson et al. |
| 5,453,171 | A | 9/1995 | Ma et al. |
| 5,531,878 | A | 7/1996 | Vadgama et al. |
| 5,534,226 | A * | 7/1996 | Gavin .............. G01N 33/4905 422/73 |
| 5,607,567 | A | 3/1997 | Yun et al. |
| 5,629,209 | A * | 5/1997 | Braun, Sr. .............. G01N 11/105 422/547 |
| 5,633,169 | A | 5/1997 | Young et al. |
| 5,731,212 | A | 3/1998 | Gavin |
| 5,821,399 | A | 10/1998 | Zelin |
| 5,869,971 | A | 2/1999 | Sherman |
| 6,060,319 | A | 5/2000 | Deetz et al. |
| 6,066,243 | A | 5/2000 | Anderson et al. |
| 6,228,652 | B1 | 5/2001 | Rodriguez et al. |
| 6,507,401 | B1 | 1/2003 | Turner et al. |
| 6,794,877 | B2 | 9/2004 | Blomberg et al. |
| 7,569,393 | B2 | 8/2009 | Sin |
| 2002/0038101 | A1 | 3/2002 | Avrahami et al. |
| 2003/0000833 | A1 | 1/2003 | Mansouri et al. |
| 2010/0029011 | A1 | 2/2010 | Sin |

OTHER PUBLICATIONS

Search Report for European Patent Application No. 03 254 082.5, mailed Oct. 11, 2010.
Office Action for U.S. Appl. No. 10/185,201, mailed Jan. 19, 2005.
Final Office Action for U.S. Appl. No. 10/185,201, mailed Sep. 7, 2005.
Office Action for U.S. Appl. No. 10/185,201, mailed Apr. 14, 2006.
Final Office Action for U.S. Appl. No. 10/185,201, mailed Dec. 21, 2006.
Office Action for U.S. Appl. No. 10/185,201, mailed Jul. 21, 2008.
Office Action for U.S. Appl. No. 12/535,589, mailed Mar. 10, 2010.
Office Action for U.S. Appl. No. 12/535,589, mailed Dec. 29, 2010.
Final Office Action for U.S. Appl. No. 12/535,589, mailed Sep. 6, 2011.
Ramamurthy, "Improved Protamine-Sensitive Menbrane Electrode for Monitoring Heparin Concentration in Whole Blood via Protamine," *Clinical Chemistry*, vol. 44, pp. 606-6113 (1998).
Operators Manual, *Hepcon® HMS Plus Hemostatis Management System; Multichannel Clot Timing Instrument With Automated Pipetting*, 116 pages, published prior to Jun. 28, 2002.

* cited by examiner

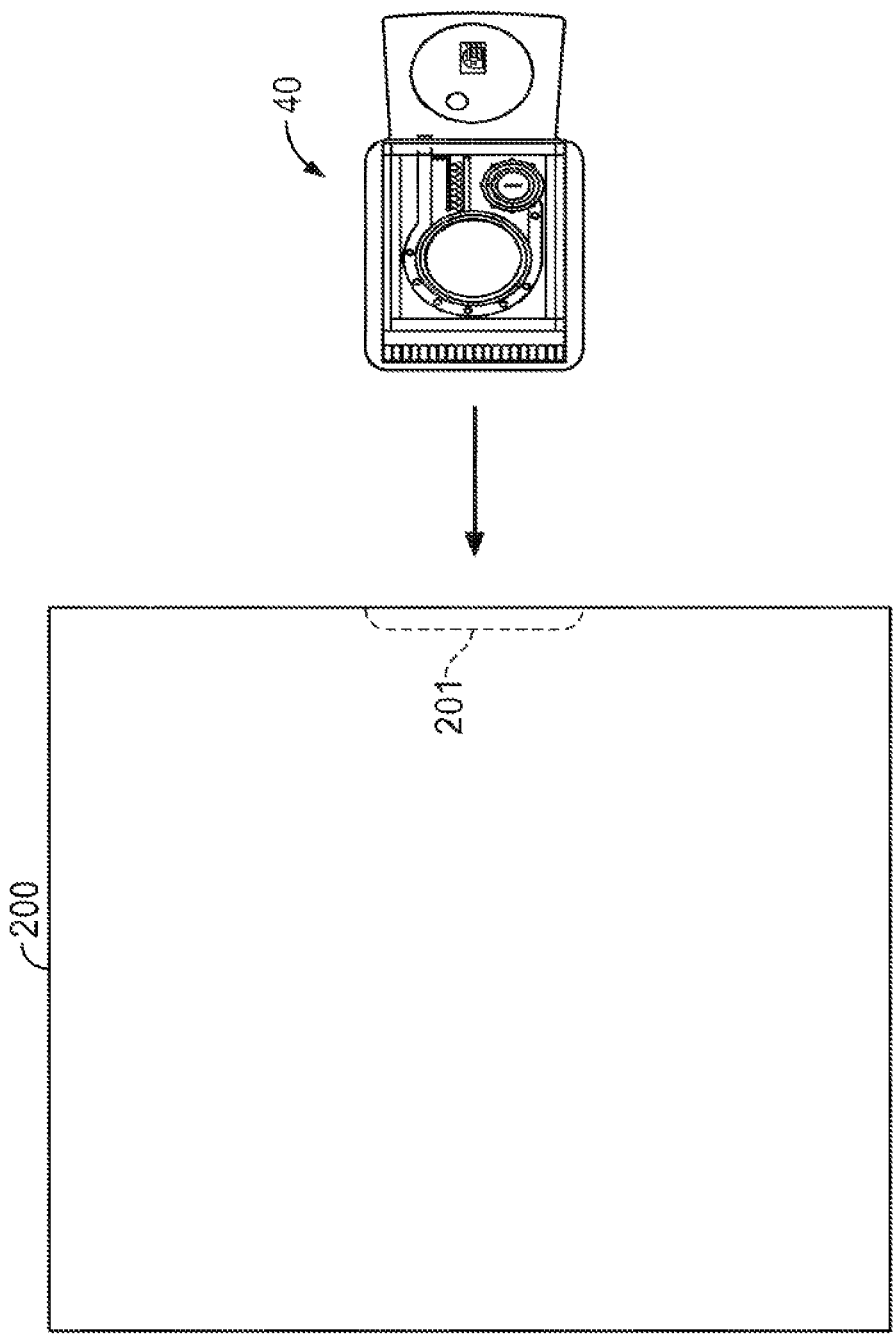

ANALYTICAL TEST CARTRIDGE; AND, METHODS

RELATED APPLICATIONS

This is a continuation of U.S. application Ser. No. 12/535,589, filed on Aug. 4, 2009, which is a continuation of U.S. application Ser. No. 10/185,201, filed Jun. 28, 2002, now U.S. Pat. No. 7,569,393, the entire disclosures of each of which are incorporated herein by reference.

TECHNICAL FIELD

The present invention relates to cartridge type test cells and methods for use with an associated analytical test instrument. The typical application of use would be in medical testing, with a liquid sample to be evaluated, for example blood, drawn from a patient. The test cell is configured to be inserted into analytical instrumentation, which can run and monitor one or more selected tests. The invention concerns improved cartridges that have structure that allows, for example, for selected, controlled conduct of a titration study with multiple locations of analysis operable to generate, if desired, a titration analysis, for example a titration curve; and, methods of analysis.

BACKGROUND

Analyses of patient fluids, for example blood, have become an increasingly important part of medicine. As a result, various analytical systems have been developed to allow for convenient sample handling and evaluation. In many instances the analytical system utilizes a portable analysis station that can be moved to various locations, for convenience. Two such analysis systems are the IRMA Blood Analysis System (IRMA), and the Blood Analysis Portal System (PORTAL), both of which are available from Diametrics Medical, Inc. of Roseville, Minn., 55113, the assignee of the present application. General features of such systems are characterized, for example, in U.S. Pat. No. 6,066,243 ('243), assigned to Diametrics Medical, Inc., the complete disclosure of which is incorporated herein by reference.

Such analysis systems are configured to utilize a removable sample cartridge for testing. The sample cartridge is typically no larger than about 10 cm. by 5 cm. (50 sq. cm.) and generally includes: a sample fluid injection port and container; various sensors for conduct of analytical analyses; various electrical leads for communication with electronic equipment within an analytical module or base station for control of analytical testing and communication of data or results; and, various mechanical structure to facilitate mounting and removal of the cartridge with respect to the analytical equipment. One such cartridge is described, for example, in U.S. Pat. No. 5,325,853 issued Jul. 25, 1994, to Diametrics Medical, Inc. as Assignee. The complete disclosure of U.S. Pat. No. 5,325,853 ('853) is incorporated herein by reference.

In general, such cartridges have relatively short useful lifetimes, with respect to the expected lifetime of the analytical componentry with which they are used. As a result, such cartridges are sometimes referred to as "disposable cartridges" or "disposable test cartridges." Indeed, in many instances, the removable cartridge is a single use cartridge.

Besides the '243 and '853 references cited and incorporated above, the assignee of the present application, Diametric Medical, Inc., is also assignee of the following U.S. patents that describe technology related to, or useable with, disposable cartridges and their use, namely: U.S. Pat. Nos. 5,384,031; 5,223,433; 6,060,319; and 5,232,667. The complete disclosure of each of the patents identified in the previous sentence is incorporated herein by reference.

Improvements in such test cartridges and analytical systems are generally sought for greater flexibility and variety in the conduct of analytical tests.

SUMMARY

According to the present disclosure, a sample analysis cartridge is provided. The cartridge includes a main flow channel, and a titration cell arrangement comprising a titration spur arrangement. The titration cell arrangement generally comprises at least one, typically a plurality, of titration spurs in fluid flow communication with the main flow channel. A typical embodiment would include at least two, usually at least three, in many instances at least four, and preferably at least six, titration spurs. In one embodiment depicted, a secondary flow channel is provided to allow for the fluid flow communication between the main flow channel and the titration spur arrangement.

Also in accord with the techniques described herein, within each titration spur is located a titration cell. In general, each titration cell includes a titration sensor arrangement including a sensor positioned in each titration cell; and, a titration reagent positioned in each titration cell.

In general, the titration cell arrangement can be operated to conduct titration studies on fluid distributed into the titration spurs and titration cells. Various approaches to conducting titration evaluations or experiments, are described.

In typical applications, each sample cartridge includes a liquid sample injection port or inlet by which a liquid sample such as blood can be injected into a main flow channel and eventually be distributed into the titration cell arrangement. The typical analysis cartridge also includes a titration cell electrical conductor arrangement positioned to provide operational electrical communication from the titration cell sensor arrangement to an analytical measurement device, when the cartridge is operatively positioned in an analytical measurement device for use.

A typical sample analysis cartridge would also include sensors in the main flow channel. These sensors can be operated to conduct further analytical evaluations on a sample being assessed.

In some systems, a single reference electrode, in the main flow channel, can be operated as a reference or counter electrode for all sensors.

The typical sample analysis cartridge has a cartridge perimeter or foot print area of no greater than about 100 sq. cm., typically no more than 80 sq. cm.; and preferably 50 sq. cm. or less. In general, the titration cell arrangement has a sample volume on the order of 100 µl (microliters) or less, with each spur and titration cell having a sample volume on the order of 10 µl or less.

In a typical configuration as characterized, each of the titration spurs in the titration cell arrangement is in a flow communication between the main flow channel, and a spur waste chamber. As a result, each titration cell is typically a flow through cell. Preferably, the fluid flow communication from the main flow channel to the titration spurs is via a secondary flow channel.

In a particular embodiment described, each titration spur is a capillary spur. By the term "capillary spur" it is meant that each titration spur is configured and sized to fill through capillary draw from a fluid source as opposed to via an alternate flow mechanism.

An example is described involving protamine as a titration agent, to titrate heparin within each titration cell, for evaluation of heparin concentration.

Methods of assembly and operation are also provided.

BRIEF DESCRIPTION OF THE DRAWINGS

FIG. 8 is a schematic view of a step of using a cartridge according to the present disclosure, in association with analytical equipment.

DETAILED DESCRIPTION

I. Typical Features of Prior Art Cartridges

Figure 1:
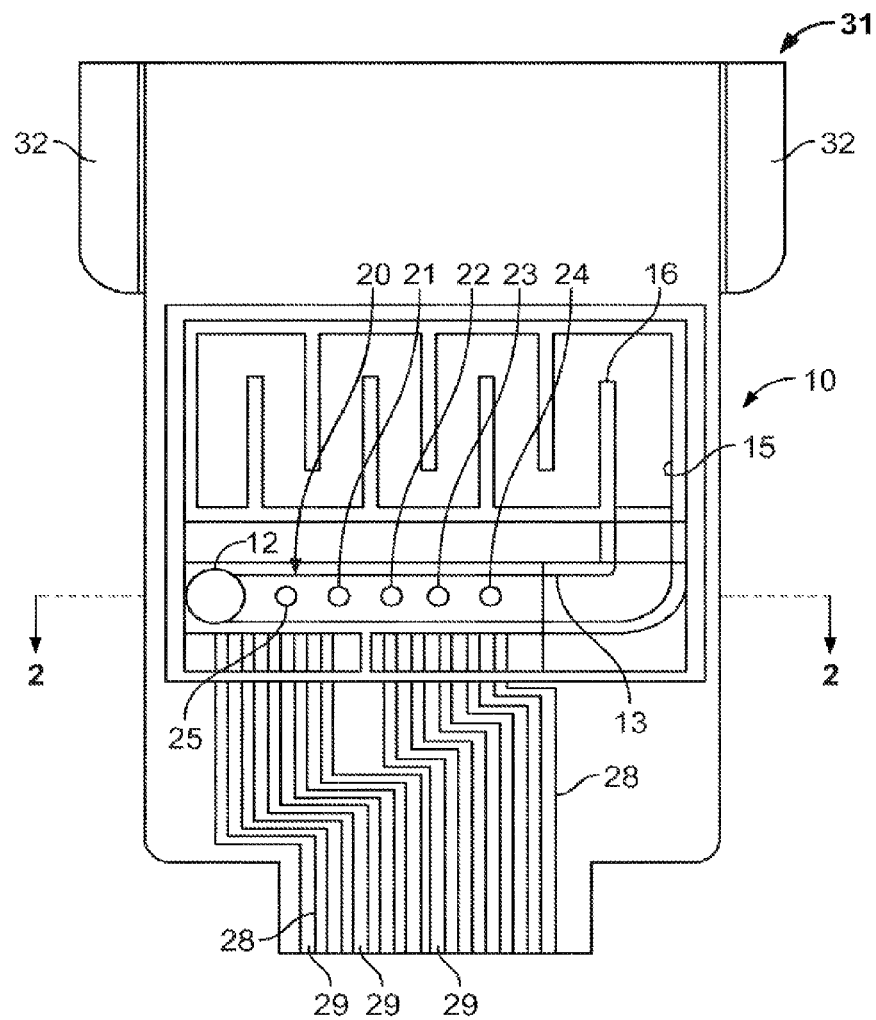
FIG. 1 is a schematic, top plan view, of a prior art disposable cartridge, according to U.S. Pat. No. 5,325,853.

In FIG. 1, a prior art cartridge 10 as described in U.S. Pat. No. 5,325,853 is depicted. In general, the cartridge 10 includes a sample inlet construction or port 12 into which a liquid sample to be evaluated can be inserted. It is anticipated that for many uses, the sample will be contained in a syringe, in which case the inlet port 12 can be provided with either a Luer-lock or other lock or engagement structure, to facilitate engagement with the syringe, for fluid transfer from the syringe into the cartridge 10 without spillage.

The cartridge 10 includes and defines a main flow chamber 13. In this instance the main flow chamber 13 is in fluid flow communication with, and extends between, the inlet 12 and an opposite fluid terminus or reservoir 15. As is described in the '853 patent, the cartridge 10 depicted includes, at fluid terminus or reservoir 15, a vane or labyrinth structure 16 to inhibit reverse fluid flow, once fluid has reached the fluid terminus 15.

Within the fluid chamber 13 is positioned an analytical sensor arrangement 20, in this instance comprising of plurality of sensors 21, 22, 23 and 24. The sensors 21, 22, 23 and 24 are typically analytical electrodes, and a reference electrode 25 is provided. Of course, a variety of types of, and variety of numbers of, sensors can be used. In general, the sensors comprise electrodes for appropriate conduct of one or more analytical determinations such as: pH evaluations; $pCO_2$ determinations, potassium ($K^+$) or other electrolyte evaluations; and, $pO_2$ evaluations. Of course, different cartridges could have different sensor types, configurations and numbers. An analytical sensor arrangement 20 comprising a reference electrode 25, a pH electrode 21, a $pCO_2$ electrode 22, a potassium electrode 23 and an $pO_2$ electrode 24, is merely an example. However, this particular collection of sensors is useful, since measurements involving the various components identified are often used and desired in blood analyses.

As indicated above, the sensor arrangement 20 will also typically include a reference electrode 25. As shown, if desired a single reference electrode 25 can be used for all of the analytical electrodes.

The cartridge 10 includes a plurality of conductive traces or conductors 28, selected ones of which terminate at associated ones of terminals or pads 29. The traces 28 provide for electrical communication to control apparatus not shown, such as an analytical module or base unit of an IRMA or PORTAL system, for control and operation of the sensor arrangement to conduct analytical measurements. The terminals 29 are generally configured for electrical contact with analytical instrumentation, when the cartridge 10 is operably positioned within analytical instrumentation, for use.

Figure 2:
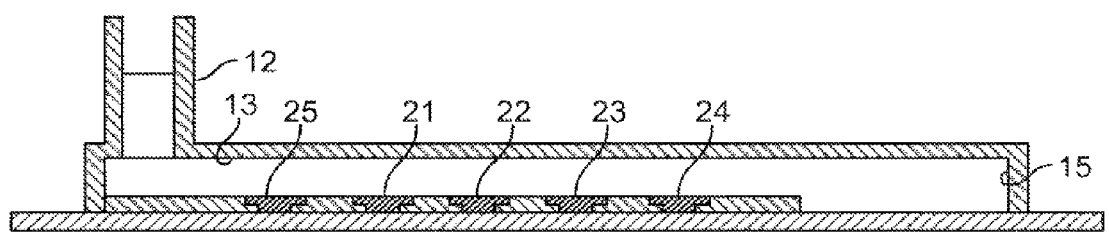
FIG. 2 is a cross-sectional view taken along line 2-2, FIG. 1.

In general, sensors 21-24 of analytical sensor arrangement 20 are positioned in the flow chamber 13, so that when patient fluid (for example blood) to be evaluated is inserted into inlet 12 and fills the flow chamber 13, each sensor 21-24 is in direct contact with the fluid, for conduct of analytical measurement. This will be understood by reference to FIG. 2, which shows the inlet 12, the main flow chamber 13, reference electrode 25 and sensors 21-24, in cross-section.

Referring again to FIG. 1, cartridge 10 includes mounting structure 31, to facilitate mounting on analytical instrumentation for use. In the instance shown, the mounting structure 31 comprises a pair of fins 32 positioned to engage a receiver structure in the analytical instrumentation, to guide the cartridge into appropriate operation position. Typically in use, the cartridge 10 is slid into a receiver in analytical instrumentation and, when the analytical determination is completed, the cartridge 10 is removed by sliding out of that instrumentation. If the cartridge 10 is for single use, it would typically then be discarded.

Systems such as the IRMA or PORTAL analytical system, using cartridges 10 as generally characterized above, are typically configured (and programmed) for use at a patient's bedside or in the immediate vicinity of the patient, to avoid the delay of collecting samples and sending them to an analytic lab. Thus, the equipment is configured for convenient operation by medical care personnel without special analytical laboratories, techniques or experience. The cartridges 10 are typically configured to be easy to handle and to fill, and the analysis equipment such as the IRMA or PORTAL equipment, is typically constructed and configured to be convenient to move, and to position in the vicinity of a patient, and to be convenient to operate.

II. An Improved Sample Analysis Cartridge.

A. General Features.

Figure 3:
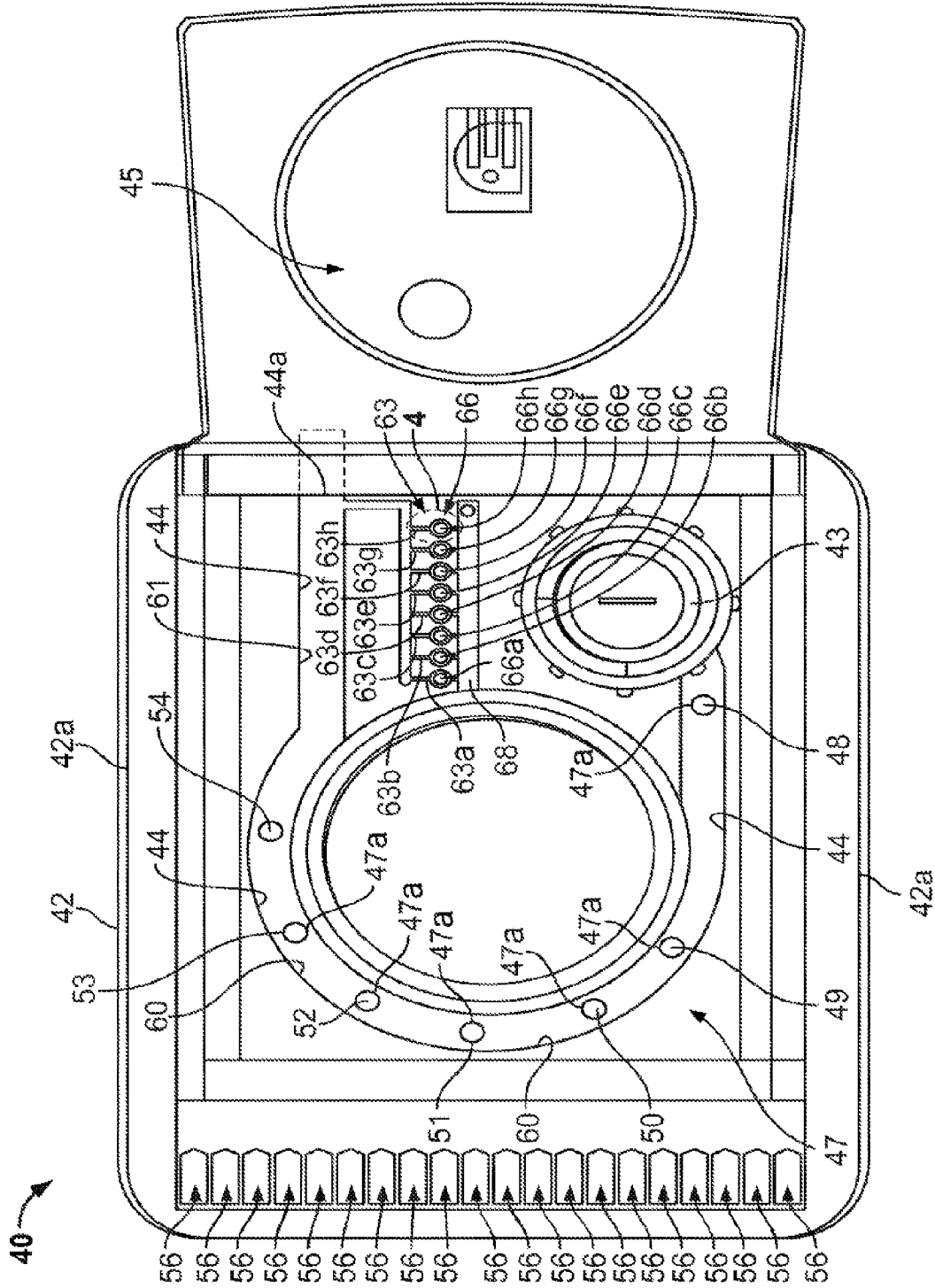
FIG. 3 is a schematic, top plan view of a cartridge according to the present invention.

Attention is now directed to FIG. 3. In FIG. 3 a schematic representation of an improved sample analysis cartridge 40 is provided. As discussed in greater detail below in section IID, except for features as described herein relating to titration spurs and cells, the cartridge 40 may have features generally as described in the co-pending U.S. patent application Ser. No. 10/160,329, filed May 30, 2002 entitled "Cartridge Arrangement, Fluid Analyzer Arrangement, and Methods;" with identification of the following as inventors: John Herbert Thornberg; Kee Van Sin; Martin Gaines Hicb; Ronald William Sand; and Scott Everett Blomberg. The co-pending application identified in the previous sentence will be referenced herein as the "Thornberg, et al. application." The "Thornberg, et al. application," is also owned by Diametrics Medical, Inc., the assignee of the present disclosure, and is incorporated herein by reference, in its entirety.

Referring to FIG. 3, the cartridge 40 generally includes a base structure 42 and includes a liquid sample injection port or inlet 43, a main flow channel or chamber 44, and a liquid terminus or waste reservoir 45. In general, the inlet 43, flow channel 44 and reservoir 45 are in fluid flow communication with one another, and can be operated similarly to the corresponding components as described above in connection with cartridge 10, FIG. 1; or in the Thornberg, et al. application. The base structure 42 may include mounting structure or flanges 42a, to facilitate mounting in analytical equipment, for use.

Cartridge 40 further includes a first analytical sensor arrangement 47, comprising sensors 47a, including one or more sensors (in this instance sensors 48, 49, 50, 51, 52 and 53), and counter or reference electrode 54. The specific number, type, order and configuration of the sensors 47a (i.e., sensors 48-53), and the reference electrode 54, is a matter of design choice, depending upon the types of analyses to be conducted within the main flow channel 44 of the analytical sensor arrangement 47. In general terms, and as an example, the sensors are selected from electrical, electrochemical, enzymatic, optical and mechanical sensors.

For example, the sensors 47a can be appropriate to determine: oxygen ($pO_2$) content, creatinine content, blood urea nitrogen (BUN) content, glucose content, sodium ($Na^+$) content, acidity (pH), carbon dioxide ($pCO_2$) content, calcium ($Ca^{+2}$) content, potassium ($K^+$) content, hematocrit (Hct), chloride ($Cl^-$) content, lactate content, coagulation evaluations and/or other desired information, depending on the particular application. Applicable principles relating to organizing sensors in a main flow channel, providing calibration materials from a calibration fluid reservoir 55, and providing valve structures to control calibration fluid or sample fluid flow, are described, for example, in the Thornberg, et al. application, again incorporated herein by reference.

The cartridge 40 includes a plurality of electrical termini 56 which are in electrical connection with traces, not shown, that communicate with, among other things, the analytical sensor arrangement 47 in the main flow channel 44, for control of the sensors 47a (i.e., sensors 48-53), during testing. In general, selected ones of the electrical termini 56 and any electrical conductivity traces that provide such a communication, will generally be referred to herein as a main flow channel "electrical conductor arrangement" positioned to provide operational electrical communication from the electrical analytical sensor arrangement 47, in the main flow channel 44, to an analytical measurement device, when the cartridge 40 is operably positioned in the analytical measurement device.

The preferred cartridge 40 depicted schematically in FIG. 3 includes a main flow channel 44 that has two primary segments: segment 60, which includes the main flow channel analytical sensor arrangement 47 therein; and, segment 61 which, in the particular embodiment shown, is free of the analytical sensors 47a.

Unlike the cartridge of the Thornberg, et al. application, cartridge 40 includes a plurality of fluid flow analytical spurs 63 in flow communication with the main flow channel 44, in particular segment 61. Herein the term "analytical spurs" when used in reference to spurs 63, refers to the fact that each spur, as described below, includes appropriate equipment for conduct of an analytical determination therein. The term "analytical spur" is meant to distinguish from a spur which provides for flow, but which does not include equipment therein for conduct of an analytical analysis.

For the particular cartridge 40 depicted, segment 60 is generally curved or arcuate, whereas segment 61 is straight; however a variety of alternative configurations is possible. Also, for the particular cartridge 40 depicted, segment 61, with which the spurs 63 are in fluid flow communication, is positioned "downstream" from the segment 60, in which the analytical sensor arrangement 47 is depicted. Alternate configurations are possible.

Referring to FIG. 3, in the particular cartridge 40 depicted, fluid flow communication between the analytical spur 63 and the main flow channel 44, in particular with segment 61 of main flow channel 44, is provided by secondary flow channel 44a. The term "secondary" in this context, is meant to refer to a flow channel branching from main flow channel 44 and which does not directly communicate to reservoir 45.

Still referring to FIG. 3, each of the spurs 63 is part of a titration cell arrangement and allows for fluid communication from flow channel 44, specifically from secondary flow channel 44a, into selected analytical titration cells 66. For the particular arrangement of spurs 63 depicted there are eight spurs 63a, 63b, 63c, 63d, 63e, 63f, 63g, and 63h; and, eight associated analytical (titration) cells 66a, 66b, 66c, 66d, 66e, 66f, 66g, and 66h, with one cell 66a-h positioned in each spur 63a-h. However, the specific number of spurs 63 and cells 66 is a matter of choice for particular experiments to be conducted, as will be apparent from the further detailed discussion.

In general, within each analytical (titration) cell 66, there is provided a sensor. The sensor is provided in electrical conduction, by conductive traces, with appropriate ones of termini 56, for operation. These conductive traces and termini are generally referred to herein as a titration cell arrangement "electrical conductor arrangement" positioned to provide operation electrical communication from the sensor arrangements of the titration cells 66, to an analytical measurement device, when the cartridge 40 is operably positioned in the analytical measurement device. It is noted that for the particular arrangement depicted in FIG. 3, the sensor of each titration cell 66 can use reference electrode 54 as the counter electrode. Alternate configurations are possible.

In general terms, a variety of types of sensors can be used for the sensors within the individual titration cells. For example, electrical, electrochemical, enzymatic, optical or mechanical sensors can be used. Typically, the same type of sensor will be used in each titration cell, of a particular titration cell set.

Herein, a spur 63 sized to be filled through capillary attraction or draw from the secondary flow channel or chamber 44a, will sometimes be referred to as a "capillary spur." Of course the spurs 63 could be sized or configured to be filled via an alternate flow mechanism.

It is noted that for the particular embodiment depicted, each of the spurs 63 communicates between the secondary flow channel 44a, and a secondary or spur waste flow channel 68; and, the configuration is such that an analytical cell 66 is positioned in each of the spurs. As a result, each analytical cell 66 can be conveniently filled by a liquid flow through the associated spur 63, and each cell 66 is, thus, a flow through cell.

In general terms, then, each of the spurs 63 is fluid flow communication with the main flow channel 44. Specifically, that fluid flow communication is provided by the secondary flow channel 44a. Also, in general each of the analytical cell 66 is a flow through cell, allowing for fluid flow from the main flow channel through the flow through cell 66, to the secondary or spur waste flow channel 68, again that flow being accommodated, in part, by the secondary flow chamber channel 44a. Herein, when it is said that one portion is in "fluid flow" communication with another portion, of the cartridge 40, a direct connection between the two, as opposed to an intermediary channel or chamber, is not meant, unless the term "direct," "directly," or a variant thereof is used.

Typically and preferably, each one of the spurs 63 has a relatively small total volume including the analytical (titration) cell volume, by comparison to the volume of the main flow channel 44. In general, what will be preferred for the size of spurs 63, is that they be sufficiently small so that:

1. When fluid is first injected into inlet 43, to fill the main flow channel 44, (and eventually secondary flow channel 44a) the pressure of injection does not force fluid into spurs 63; and
2. Fluid will eventually flow into the spurs 63 through wicking, capillary attraction, or a similar mechanism.

The particular cells 66 depicted are circular, each preferably having: a diameter of 0.08 cm. or less, typically 0.05 cm. or less; and, a depth of 0.05 cm. or less, typically 0.03 cm. or less. Typically, each cell is constructed to have a volume of 2.5 µl or less; typically, 1 µl or less. Preferably, the volume of each is 0.4 µl or less.

It is noted that in a commercial product involving a titration set of cells or spurs as characterized (for analysis of a selected known analyte, with a selected known reagent), the titration cell arrangement can be configured, and the analytical instrumentation used with the cartridge 40 can be programmed and configured, based upon empirically derived data; i.e., data developed (for example, by the equipment manufacturer) based on studies with standards, to facilitate the analytical analysis.

It is foreseen that in a typical application, the cross-sectional area of each one of the spurs 63, in a region immediately adjacent secondary flow channel 44a, and referring to the cross-section perpendicular to the flow path, would be on the order of about 0.4 cm² or less, typically about 0.1 cm² to 0.2 cm². In general, the spurs 63 define a flow path between secondary flow chamber 44a and secondary or spur waste flow terminus or chamber 68, with the flow path extending through and filling the analytical cells 66.

Figure 4:
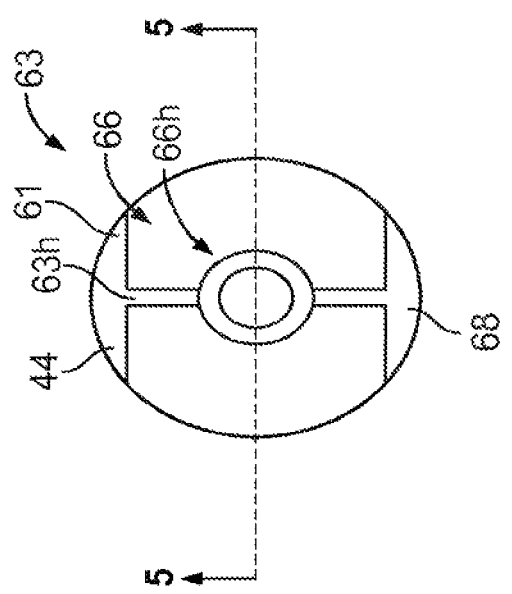
FIG. 4 is an enlarged, fragmentary, schematic view of a portion of the arrangement shown in FIG. 3.

In FIG. 4, an enlarged fragmentary schematic plan view of one of the spurs 63 (specifically spur 63h) and an associated analytical cell 66 (specifically 66h) from FIG. 3, is depicted.

Figure 5:
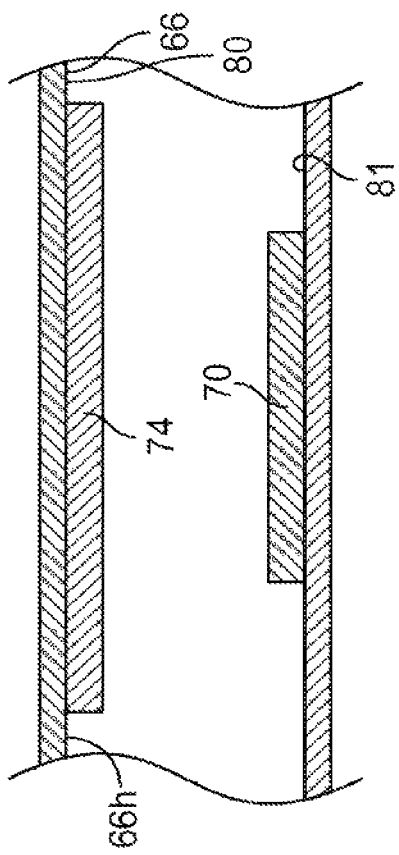
FIG. 5 is a fragmentary cross-sectional view taken along line 5-5, FIG. 4.

Attention is now directed to FIG. 5, which is a side cross-sectional view taken through cell 66h generally along line 5-5, FIG. 4. Referring to FIG. 5, in general the cell 66 includes a sensor 70 which is provided in electrical communication with appropriate ones of termini 56 for operation. Cell 66 also includes a reagent or titration agent 74 for use, as described below.

It is anticipated that each of a selected plurality (and in some instances all) of the analytical (titration) cells 66, of a given set, would have a similar construction namely: a sensor 70; and, a reagent 74. The size and type of sensor 70 and type and amount of reagent 74 will be selected depending on the particular analytical determination(s) (typically a titration) to be made with the analytical cells 66.

In general, the cells 66 and the spurs 63 can be used for controlled analytical experiments for which, in general: (i) it is desired to have a plurality of small cells that can be operated simultaneously (or within a relatively short period of time of one another), and without sample refilling, to conduct analytical determination(s); and, (2) for which it is acceptable to have an operation with small, (typically less than 1 µl) cells 66 that can be easily filled, but for which problematic diffusion into and out of the cells 66 during conduct of the experiment, is not desired.

Herein the term "problematic diffusion" (and variants thereof) when used in this context is meant to refer to an amount of diffusion that would interfere with the conduct of the analytical evaluation desired, in each cell. By the term "problematic diffusion" it is not necessarily meant that no diffusion occurs, but rather that any amount which occurs in the time period of the experiment conducted, is within the controlled parameters of the experiment and does not typically interfere with the ability to obtain accurate, reproducible, analytical results. With relatively small spur cross-sectional areas and volumes, and small titration cell volumes, as characterized herein, the total amount of diffusion during the conduct of an experiment would typically be acceptably low, or for all practical purposes, negligible. Of course, in some instances, the relatively small amount of diffusion which does occur, can be managed through empirical observations and calculations which will cancel out its effect.

As will be apparent from the following descriptions, the arrangement of spurs 63 and cells 66 is particularly appropriate for conduct of titration experiments. When selected ones of the cells 66 and spurs 63 are configured for a titration experiment, the selected cells will be generally referred to as herein as a "titration set" of cells or spurs; with the cells sometimes referenced as "titration cells" and with the spurs sometimes referenced as "titration spurs." Typically, a titration set will include at least two cells, usually at least three cells, typically at least four cells, and preferably at least six cells, for example six to ten cells. Typical operation of such a titration set, will be apparent from the following.

B. A Typical Operation to Perform a Controlled Titration Experiment.

Advantages from features characterized above for cartridge 40, will be apparent from the descriptions in this section, of a typical (hypothetical) titration experiment. For purposes of this description, assume that the liquid to be evaluated is blood, and that a titration is to be performed to evaluate an analyte ($A_B$) in the blood. Assume also that the analyte is analyte "A", which can be detected by an analyte sensor 70 in each cell operated as part of the experiment. Assume also that the analyte is one which can be titrated with a reagent (R), 74, in this instance used as a titrating agent "T", and that titrated analyte, referenced as AT, is not detectable by the analyte sensor.

The plurality of analytical cells 66, can be operated as titration cells, to define a titration curve or other titration calculation (analysis), provided at least the following are established:

1. An appropriately defined, and preferably equal, volume for each of the involved titration cells 66 (by "equal" in this context it is meant that preferably the volume of each cell 66 is within 5% of a selected volume or selected titration cell volume);
2. A different amount of titration agent "T," i.e., agent 74, is provided in each one of at least selected titration cells, with distribution among the selected cells including at least two cells, typically at least four cells, and preferably at least six cells, in which the amount of active titration agent T is different and is less, on an equivalent basis, than the amount of analyte A (in the cell) to be determined; and
3. The spurs 63 are sufficiently small so as to inhibit problematic diffusion of analyte and/or titration agent into, or out of, the cells 66 during conduct of the titration.

Figure 6:
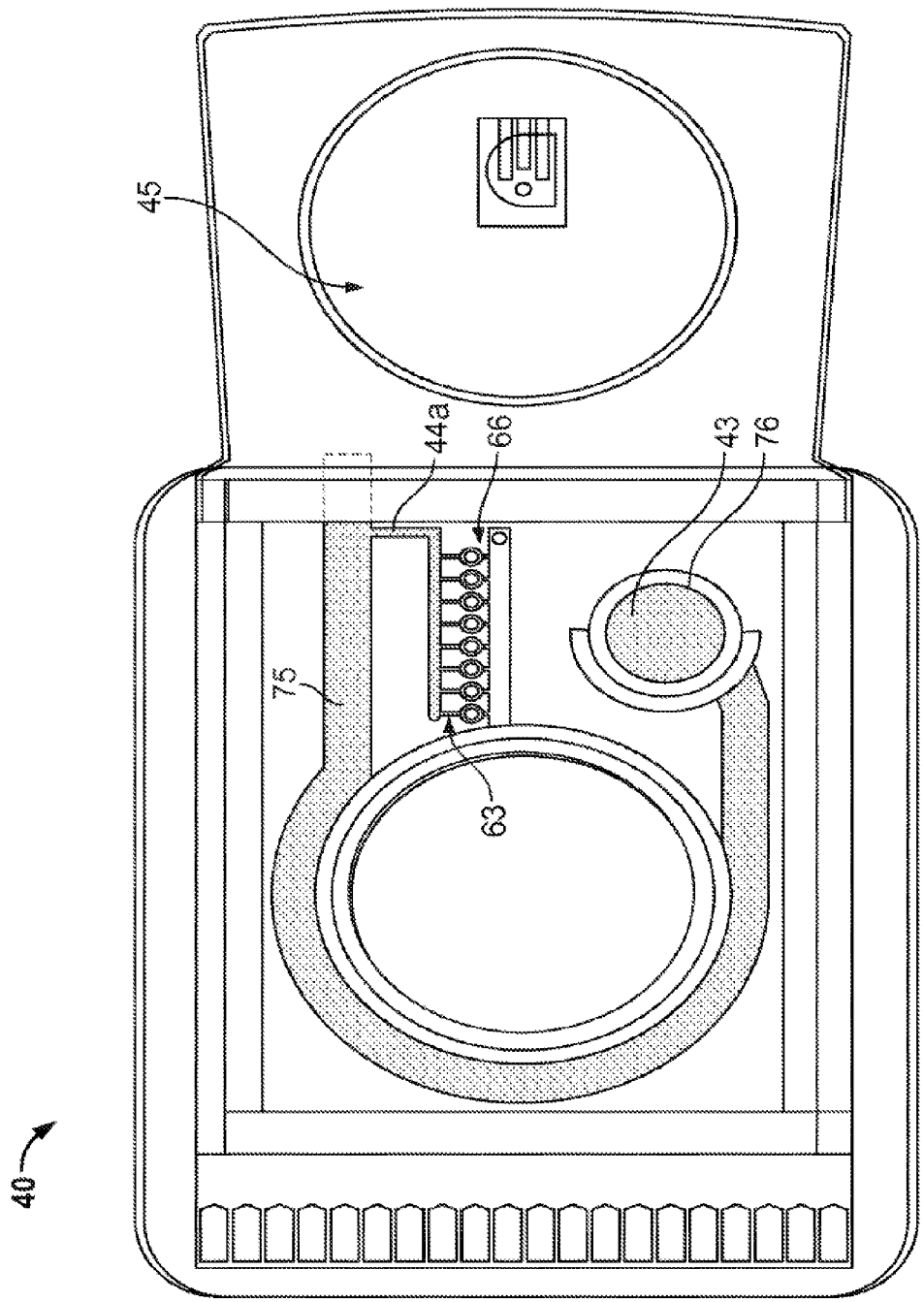
FIG. 6 is a view analogous to FIG. 3, depicted during a first stage of providing a liquid sample therein.

For conduct of such an operation, blood 75, FIG. 6, would be inserted into cartridge 40 through inlet 43; typically, with the liquid insertion volume being enough to fully fill the main flow channel 44, as indicated in FIG. 6. Indeed, in FIG. 6, adequate blood flow is provided to not only fill the flow channel 44, but also to flow into the main flow waste reservoir 45 (and possibly also into channel 44a). The stage of filling the main flow channel 44 by insertion of fluid (for example blood) is referred to herein as the first stage of filling or first stage of fluid flow. In this stage, although the fluid flow is into the main flow channel 44 and at least to some extent also the secondary flow channel 44a, due to the small size of the spurs 63, the spurs 63 are generally not immediately filled by the insertion operation. (In FIG. 6, syringe 76 is shown attached to the inlet 43.)

Figure 7:
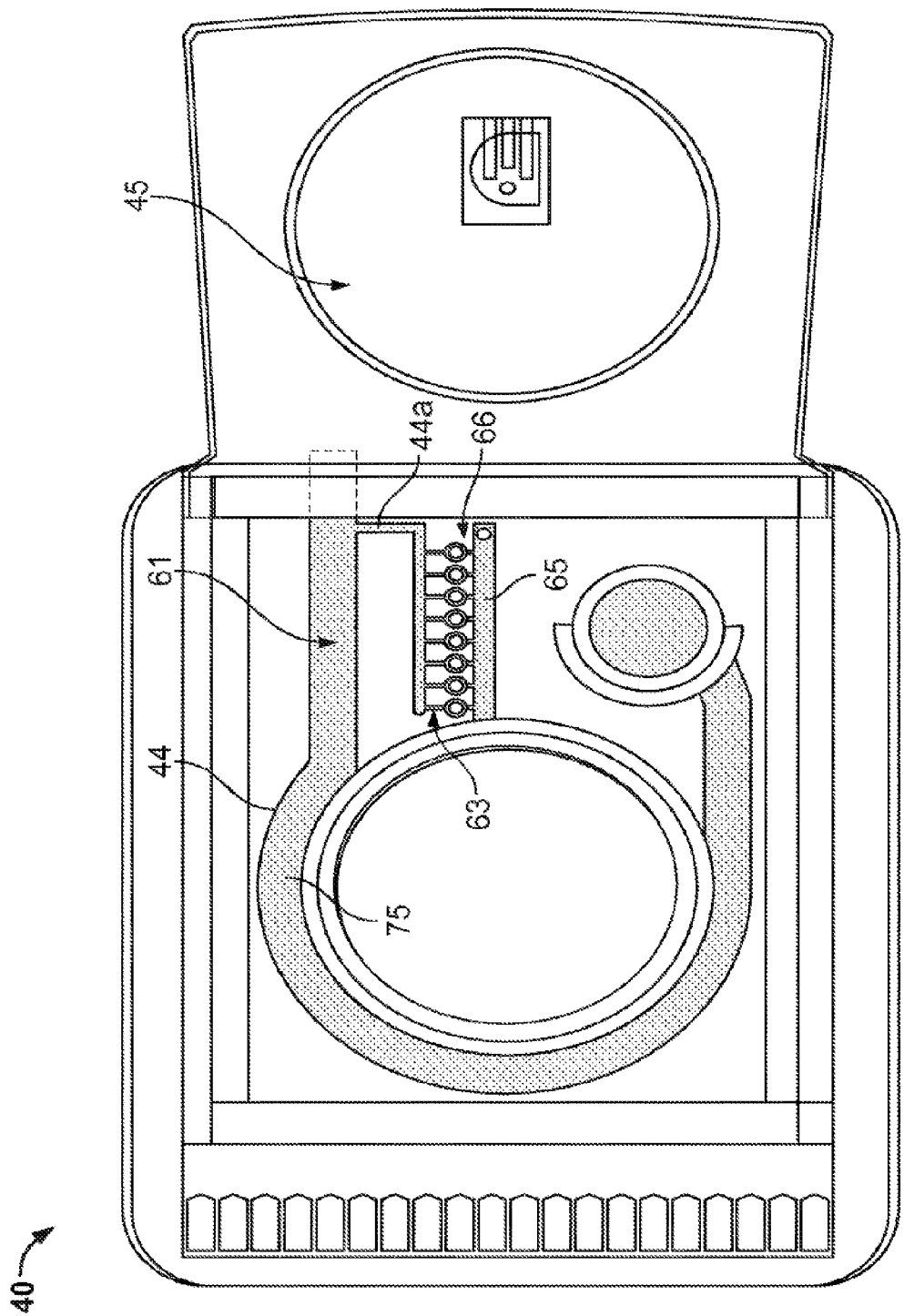
FIG. 7 is a view analogous to FIG. 3, depicted during a second stage of providing a liquid sample therein.

In time, through capillary action, wicking or similar action, blood (sample liquid) flow will have gone through the spurs 63 to fill the analytical cells 66. This is shown in FIG. 7 and is characterized herein as a second stage of liquid flow. When the blood enters the analytical cells 66, reagent "R" or titration agent "T", pre-positioned in the selected cells 66, will dissolve into the blood and react, or if it is not soluble it will act upon (react with) the blood. Upon dissolution into, or contact with, the blood, the titrating agent "T" will titrate the analyte "A," to AT. AT, of course, was defined as non-detectable by the sensor 70. Since different amounts of titration agent "T" are positioned in different cells, the amount or extent of titration to AT will vary among selected ones of the various selected cells, as long as there is not an excess of agent T. After an appropriate time has been allowed for the cell 66 to fill with blood, and the titration to occur, the analyte sensor 70 can be operated to conduct a titration analysis and to determine the amount, or relative amount, of remaining analyte "A" in each selected cell.

Appropriate programming can be provided in analytical equipment utilized in association with a cartridge 40, such that with appropriate knowledge such as the amount of titration agent "T" in each cell, and about the size of the cells (or that the various cell 66 are the same volume), a titration analysis (calculation) or curve for the analyte "A" can be calculated or defined. From this the amount (or concentration) of analyte "A" in the blood sample, can be calculated or extrapolated.

Herein when it is said that a titration curve or amount can be "calculated or defined" it is not meant that a curve is necessarily plotted or presented by the analytical equipment. The titration calculation can be the result of conduct of a programmed mathematical function within the programming of the analytical equipment, used to calculate or define certain data points.

The assembly or cartridge 40 can be operated to accomplish a variety of titrations. An example would be a heparin titration, using protamine. For such an operation, the analyte A would typically be the heparin; and the reagent (R) or titration agent T would typically be the protamine. The sensor 70 would then be a heparin sensor. Heparin specific sensors are known; see for example U.S. Pat. No. 5,236,570, incorporated herein by reference.

In an alternate form of the same type of experiment, sensor 70 could be configured as a sensor for the reagent or titration agent T (i.e., the protamine), in which case excess agent (i.e., protamine) in different amounts (due to different amounts of excess protamine) would be used, in the analytical cells 66. In this instance, when the blood dissolves the protamine, or otherwise is acted upon by the protamine, the heparin would titrate, in each cell, the same amount of protamine. The sensors in different cells would then detect the varying amounts of protamine remaining, to define a titration curve, (or allow conduct of a titration analysis) for the protamine. From the titration analysis for the protamine, the amount or concentration of heparin could be calculated.

In the experiment described in the previous paragraph, with respect to the actual analytic evaluation conducted in the cell 66, the heparin would be the titration agent T, and the protamine would be the analyte A. In this instance, of course, the analyte A would be an experimental analyte $A_E$, used to eventually allow for calculation of the amount of blood analyte ($A_B$) (i.e., heparin) being evaluated.

In still a further alternate of the experiment, the cells 66 could be configured so that the detectable species within each analytical cell, detectable by the sensor, is the titrated analyte, AT, for example $A_B T$ for blood analyte. In such a situation, the experimental analyte ($A_E$) detected would be the titrated species AT. Its concentration could then be used to calculate the concentration of the blood analyte $A_B$ originally present.

In general terms, there is provided a method of defining an analyte presence in a liquid sample, the method including steps of: (a) directing a liquid sample into a plurality of spurs and fluid flow communication with a single main flow channel; (b) titrating at least one of the selected analyte and a selected reagent in the liquid sample to a different degree in selected ones of the plurality of the spurs; and, (c) calculating (by conduct of a titration calculation or analysis) an amount of analyte to be determined in the liquid sample based on a titration analysis determined by the step of titrating.

As characterized in the previous paragraph, the method would apply whether the actual analyte determined in the cell 66, by the sensors therein, was a blood analyte, a reagent analyte, or a titration analyte resulting from a combination of the reagent and the blood analyte.

Of course, the techniques described herein can be used for titration of a variety of analytes, heparin is merely presented as an example. The titration approach is particularly useful in instances where the analyte to be determined is presented in an amount, or over a range, that cannot be readily managed for analysis through a typical conventional single sensor arrangement, with acceptable accuracy and reproducibility. A titration approach, in effect, allows for controlled reduction in the amount of the analyte involved, to a more controlled amount and/or range, for effective analytical evaluation.

C. Variations in Titration Experiment and Configuration.

Now that general operation of a titration experiment in an assembly according to the present invention is understood, some variations possible in the arrangement to facilitate operation are provided.

First, and referring to FIG. 1, for a typical operation of a titration, at least two titration cells, usually at least three cells, and typically at least four cells, in the titration cell set or arrangement will be used. It will be preferred to use at least six cells, typically six to ten cells, for a given titration experiment.

Of course, the amount of reagent 74 or titration agent in each titration cell will be selected based upon: anticipated range of blood analyte to be evaluated; and, an adequate range of data points to ensure accurate titration calculations. For commercial products, the preferred amount of reagent in each cell will typically have been determined through extensive empirical evaluations based on reference samples and studies. In general, at least two, usually at least three, and typically at least four and preferably at least six, of the titration cells will include amounts of reagent that differ in terms of total equivalents for reaction with blood analyte or other sample analyte (and thus concentration). The difference in amount of reagent among the cells needs to be adequate for conduct of the desired analysis, for example a titration. The term "adequate" and variants thereof, in this context, is meant to refer to enough difference to support the intended measurement or calculation. The difference in equivalents will preferably be at least 5% (by equivalents concentration) with respect to one another, typically at least 10%. As a result of adequate differences, in reagent amount, the titration proceeds to a different amount, or degree, in selected ones of the cells.

In a typical selected titration experiment, all sensors in titration cells operated as part of a selected experiment, will be operated simultaneously, using the same counter or reference electrode, to generate data for evaluation of the titration curve calculation or other titration analysis. However, there is no specific requirement that the sensors for the titrations in all selected cells be simultaneously operated or that a single reference electrode be used. For example, operation of the cells may be sequenced or operated with some simultaneously and others at a separate points in time. It is foreseen that in typical preferred processes, a titration analysis will be conducted such that all sensors operated as part of that analysis are evaluated in a total elapsed time, from the first measurement taken in the first titration cell, to the last measurement taken in the last titration cell, of no more than 10 minutes and preferably no more than 3 minutes.

Of course, cartridge 40 can be configured for conduct of more than one type of titration experiment. Thus, a first set of titration cells could be set up for first titration experiment; with a second set of titration cells set up for a second titration experiment.

Within any selected titration set of titration cells, generally the same titration agent (reagent) and analyte sensor will be located in each titration cell; however, the amount of the reagent or titration agent may be varied among the cells. In some instances, however, the same amount of reagent (titration agent) may be used in more than one cell, to obtain multiple points of data for accuracy.

In FIG. 5, the titration agent 74 is shown affixed (for example before dissolution) to a surface 80 of the cell 66 opposite from a surface 81 at which the analyte sensor 70 is located. In some embodiments, the two could be positioned on the same surface or even in contact with one another.

D. Typical Materials and Methods of Assembly.

In section IIA-IIC, specific detail in techniques directly related to configuration and operation (conduct) of titration experiment, were provided. In this section other general descriptions relating to the cartridge 40 are provided. The information is intended to be general in nature, and is analogous to that found in the Thornberg, et al. application, again incorporated herein by reference.

In general, the sensors (47a, 70) may be of a variety of types. Ones typically utilized as sensors in cartridges according to the present disclosure, are selected from: ion selective electrode (potentiometric) sensors; amperometric sensors; conductometric sensors; and enzymatic sensors.

If the fluid sample is blood, for the sensors in the main flow channel 44, typically usable constructions include ion selective electrode sensors to measure pH and $pCO_2$. With current technology, a $pO_2$ sensor would typically be an amperometric sensor. For blood electrolytes, for example, sodium ($Na^+$) sensors, calcium ($Ca^{+2}$) sensors and potassium ($K^+$) sensors, ion selective electrode sensors are typically used. Hematocrit may be measured by using, for example, a conductometric sensor. Chloride ($Cl^-$) can be measured, in typical implementations, with an ion selective electrode sensor. Glucose, blood urea nitrogen (BUN) and creatinine are typically measured using enzymatic sensors. Measurements of blood coagulation are typically conducted using conductometric sensors.

For the example described in the titration experiment, of a heparin sensor, typically an ion selective sensor would be used.

In many instances, for the various sensors, calibration evaluations will be conducted. Descriptions of techniques for conducting calibration evaluations are provided for example in U.S. Pat. No. 5,325,853, again incorporated herein by reference, and in the Thornberg, et al. application, again incorporated herein by reference.

In some instances it may be desirable to store certain types of sensors in contact with solution ("wet-stored"), or separate from solution ("dry-stored"). Techniques for creating selected fluid flow or location, and valve control over fluid flow, are described in the Thornberg, et al. application, incorporated herein by reference.

If the titration cells include a soluble agent or titrating agent, it will generally be desired that the titration cells be maintained empty of solvent, until use. If there is also to be liquid in part of the main flow channel, adaptable valving techniques and channel design techniques to leave portions of the main flow channel 44 (or portions in communication with the main flow channel 44) dry, such as portion 44a, are described in the Thornberg, et al. application.

A typical cartridge 40 comprises a multi component structure including: a base structure or housing; and, an enclosed analytical substrate. The housing would typically comprise molded plastic components, for example polycarbonate components. The analytical substrate would typically comprise a ceramic substrate having deposited thereon: appropriate electrically conductive materials for formation of the sensors and electrical traces; and any needed chemical or enzyme materials, for operation of the various sensors and cells. The typical cartridge would comprise snap-together components, or adhesively secured components. Dimensions for a typical cartridge would typically be no more than 100 sq. cm., and usually no more than 80 sq. cm., for example 50 sq. cm. or less, as a cartridge perimeter or foot print area, and with a total height (not including an injection syringe) of typically no greater than about 3 cm.

The molded plastic components would include appropriate molded paths or vanes to define the various internal structure such as flow channels, spurs and cells.

A typical cartridge would be configured to hold, during operation, a total fluid sample having a volume of no greater than about 3 milliliters (ml), and typically no more than about 200 microliters. The total sample volume within the main flow channel and spurs, during conduct of analytical evaluations, for a typical experiment would typically be no more than 100 microliters, usually no more than 80 microliters, and typically no more than 50 microliters. The total fluid volume in the titration spurs and cells would typically be no more than 20 µl.

Attention is now directed to FIG. 8, which is a schematic depiction showing the step of using equipment as characterized herein. Referring to FIG. 8, analytical equipment or base station equipment is indicated generally at 200. The equipment includes a receiver 201, receiving cartridge 40 in accord with the disclosure herein. The equipment 200 would be configured and programmed, for electrical communication with the cartridge 40, for conduct of an analytical analysis, for example a titration calculation, as characterized hereinabove. The equipment 200, for example, could be variations of the currently commercially available IRMA or PORTAL systems, modified with appropriate programming and/or equipment to control titration evaluations using the cartridge 40.

Above, various configurations, structures and techniques, for an improved sample analysis cartridge have been provided. The disclosure is meant to provide information for preparation of a variety of examples, and is not meant to be limiting to any specific configuration or application.

What is claimed is as follows:

1. A method of assaying an analyte presence in a liquid sample, the method comprising:

directing a liquid sample into a plurality of capillary spurs in fluid flow communication with a single main flow channel, each capillary spur including a titration cell from a plurality of titration cells, each titration cell from the plurality of titration cells containing a sensor, each titration cell being a flow-through titration cell;

titrating a first quantity of a reagent into a first titration cell from the plurality of titration cells;

titrating a second quantity of the reagent into a second titration cell from the plurality of titration cells; and calculating an amount of an analyte in the liquid sample based, at least in part, on the first quantity of the reagent and the second quantity of the reagent.

2. A method according to claim 1 wherein:
the analyte is heparin; and
the liquid sample is blood.

3. A method according to claim 1 wherein:
directing the liquid sample includes directing the liquid sample into an analytical sample cartridge having a total perimeter area of no more than 100 sq. cm.

4. A method according to claim 3 wherein:
the plurality of titration cells includes at least six titration cells each of the at least six titration cells including at least one of at least six sensors; and
calculating the amount of the analyte is based, at least in part, on a signal from each of the at least six sensors.

5. A method according to claim 1 wherein:
the analyte is heparin;
the liquid sample is blood; and
the reagent is protamine.

6. The method according to claim 1, further comprising directing the liquid sample from each flow-through titration cell into a waste flow channel.

7. The method according to claim 1, further comprising injecting the liquid sample into the single main flow channel, each capillary spur sized such that a pressure of injecting the liquid sample into the single main flow channel does not force fluid into each capillary spur.

8. The method according to claim 7, wherein directing the liquid sample into the plurality of capillary spurs is accomplished through capillary action.

9. The method according to claim 1, wherein the first quantity of a reagent is titrated into the first titration cell prior to the liquid sample being directed into the plurality of capillary spurs.

* * * * *